United States Patent [19]

Meyer et al.

[11] Patent Number: 5,550,220
[45] Date of Patent: Aug. 27, 1996

[54] ALKYL GLYCOSIDE FATTY ACID POLYESTER FAT SUBSTITUTE FOOD COMPOSITIONS AND PROCESS TO PRODUCE THE SAME

[75] Inventors: Richard S. Meyer, Federal Way; Michael L. Campbell, Kent, both of Wash.; Daryl B. Winter, San Bruno, Calif.; Jeffrey M. Root, Tacoma, Wash.

[73] Assignee: Curtice-Burns, Inc., Rochester, N.Y.

[21] Appl. No.: 359,942

[22] Filed: Dec. 20, 1994

Related U.S. Application Data

[63] Continuation of Ser. No. 869,288, Apr. 15, 1992, abandoned, which is a continuation-in-part of Ser. No. 770,771, Oct. 4, 1991, abandoned, which is a continuation of Ser. No. 368,675, Jun. 19, 1989, abandoned, which is a continuation-in-part of Ser. No. 347,264, May 3, 1989, Pat. No. 4,942,054, which is a continuation-in-part of Ser. No. 122,188, Nov. 18, 1987, Pat. No. 4,840,815, which is a continuation-in-part of Ser. No. 49,625, May 13, 1987, abandoned, said Ser. No. 869,288, is a continuation of Ser. No. 347,264.

[51] Int. Cl.⁶ .............................. C07G 3/00; C07H 1/00; C07H 13/06; C07H 15/04
[52] U.S. Cl. .................. 536/18.5; 536/18.6; 536/119; 536/120; 536/124; 426/106; 426/658; 426/804
[58] Field of Search .................. 536/18.6, 18.5, 536/119, 120, 124; 426/106, 658, 804; 514/23

[56] References Cited

U.S. PATENT DOCUMENTS

| | | | |
|---|---|---|---|
| 2,759,923 | 8/1956 | Gibbons | 536/18.2 |
| 2,831,854 | 4/1958 | Tucker et al. | 536/119 |
| 2,931,797 | 4/1960 | Gibbons et al. | 536/116 |
| 3,096,324 | 7/1963 | Goins et al. | 536/119 |
| 3,219,656 | 11/1965 | Boettner | 536/18.3 |
| 3,248,381 | 4/1966 | Nobile et al. | 536/119 |
| 3,249,600 | 5/1966 | Nobile et al. | 536/119 |
| 3,251,827 | 5/1966 | Schnell et al. | 536/119 |
| 3,347,848 | 10/1967 | Ismail et al. | 536/119 |
| 3,547,828 | 12/1970 | Mansfield et al. | 252/351 |
| 3,558,597 | 1/1971 | von Brachel et al. | 536/119 |
| 3,597,417 | 8/1971 | Myhre | 354/1 |
| 3,598,865 | 8/1971 | Lew | 536/18.6 |
| 3,600,186 | 8/1971 | Mattson et al. | 536/119 |
| 3,625,706 | 12/1971 | Myhre | 426/601 |
| 3,634,397 | 1/1972 | Thompson et al. | 536/119 |
| 3,707,535 | 12/1972 | Lew | 536/18.6 |
| 3,714,144 | 1/1973 | Feuge et al. | 536/119 |
| 3,729,461 | 4/1973 | Pomeranz et al. | 536/18.6 |
| 3,772,269 | 11/1973 | Lew | 536/18.6 |
| 3,839,318 | 10/1974 | Manfield | 536/18.6 |
| 3,963,699 | 6/1976 | Rizzi et al. | 536/119 |
| 4,005,195 | 1/1977 | Jandacek | 514/23 |
| 4,349,669 | 9/1982 | Klahr et al. | 536/127 |
| 4,368,213 | 1/1983 | Hollenback et al. | 426/590 |
| 4,382,924 | 5/1983 | Berling et al. | 536/119 |
| 4,461,782 | 7/1984 | Robbins et al. | 426/549 |
| 4,517,360 | 5/1985 | Volpenhein | 536/119 |
| 4,518,722 | 5/1985 | Volpenhein | 536/119 |
| 4,611,055 | 9/1986 | Yamamoto et al. | 536/119 |
| 4,713,447 | 12/1987 | Letton | 536/186 |
| 4,721,781 | 1/1988 | Rowton | 536/4.1 |
| 4,797,300 | 1/1989 | Jandacek et al. | 426/549 |
| 4,810,516 | 3/1989 | Kong-Chan | 426/548 |
| 4,840,815 | 6/1989 | Meyer et al. | 426/611 |
| 4,942,054 | 7/1990 | Winter et al. | 426/601 |
| 4,952,687 | 8/1990 | Bodor et al. | 536/119 |
| 4,973,489 | 11/1990 | Meyer et al. | 536/115 |

FOREIGN PATENT DOCUMENTS

| | | |
|---|---|---|
| 0233856 | 2/1987 | European Pat. Off. . |
| 0236288 | 2/1987 | European Pat. Off. . |
| 0254376 | 1/1988 | European Pat. Off. ........ C07H 13/06 |
| 0256585 | 2/1988 | European Pat. Off. ........ C07H 13/06 |
| 0304131 | 2/1989 | European Pat. Off. ........ A23D 3/00 |
| 0304130 | 2/1989 | European Pat. Off. ........ A23D 3/00 |
| 0301634 | 2/1989 | European Pat. Off. ........ C07H 13/06 |
| 156263 | 9/1982 | Germany . |

OTHER PUBLICATIONS

D. J. Hamm, "Preparation and Evaluation of Trialkoxytricarballylate, Trialkoxycitrate, Trialkoxyglycerlether, Jojoba Oil and Sucrose Polyester as Low Calories Replacements of Edible Fats and Oils," *Journal of Food Science*, vol. 49 (1984).

*Primary Examiner*—John Kight
*Assistant Examiner*—Everett White
*Attorney, Agent, or Firm*—Christensen, O'Connor, Johnson & Kindness PLLC

[57] ABSTRACT

A method for producing alkyl glycoside polyesters comprising admixing a lower acyl ester alkyl glycoside, a fatty acid lower alkyl ester, and an alkaline metal catalyst to form a reaction mixture. Thereafter, the reaction mixture is heated to a reaction temperature and maintained at that temperature for a predetermined period of time. A low vacuum is drawn over the mixture. Yields of on the order of 95% to 99% can be achieved in accordance with this method. Novel fat substitute food compositions containing alkyl glycoside fatty acid polyesters are produced in accordance with this present invention. The alkyl moiety may be unsubstituted or substituted by from 1–3 free hydroxyl groups or fatty acid esterified hydroxyl groups.

29 Claims, No Drawings

ALKYL GLYCOSIDE FATTY ACID POLYESTER FAT SUBSTITUTE FOOD COMPOSITIONS AND PROCESS TO PRODUCE THE SAME

CROSS-REFERENCE TO RELATED APPLICATIONS

This is a continuation of prior application Ser. No. 869,288, filed Apr. 15, 1992, now abandoned, which is a continuation-in-part of: (a)prior application Ser. No. 770,771, filed Oct. 4, 1991, now abandoned, which is a continuation of prior application Ser. No. 368,675 filed Jun. 19, 1989, now abandoned, which was a continuation-in-part of prior application Ser. No. 347,264, filed May 3, 1989, now U.S. Pat. No. 4,942,054, which was a continuation-in-part of prior application Ser. No. 122,188, filed Nov. 18, 1987, now U.S. Pat. No. 4,840,815, which was a continuation-in-part of prior application Ser. No. 049,625, filed May 13, 1987, now abandoned; and is also a continuation-in-part of (b) prior application Ser. No. 532,926 filed Jun. 4, 1990, now abandoned, which is a continuation of prior application Ser. No. 347,264, filed May 3, 1989, now U.S. Pat. No. 4,942,054, which was a continuation-in-part of prior application Ser. No. 122,188, filed Nov. 18, 1987, now U.S. Pat. No. 4,840,815, which was a continuation-in-part of prior application Ser. No. 049,625, filed May 13, 1987, now abandoned, the benefit of each filing date which is hereby claimed under 35 U.S.C. §120.

TECHNICAL FIELD

The present invention relates to fat substitute food compositions, and more particularly to alkyl glycoside fatty acid polyester fat substitute food compositions and processes for producing the same.

BACKGROUND OF THE INVENTION

One of the most common nutritional problems in the United States today is obesity. In general, obesity results from the consumption of more calories than are expended. Fats contribute from 30% to 40% of the total calories consumed by most Americans. Consumption of fat is related to many disease states, such as heart disease. Successful reduction of fat consumption has not been achieved because of the dietary habits of many industrialized nations. Therefore, the search for fat substitutes or low calorie fats has attracted considerable attention in recent years.

Among the possible low calorie fats or fat substitutes synthesized to date are: sugar polyesters, sugar alcohol polyesters such as sucrose polyesters (SPE), polyglycerol esters, neopentyl-type alcohol esters, glycerol dialkyl ethers, triglyceride esters of alpha substituted carboxylic acids, diglyceride esters of short-chain dibasic acids, trialkoxytricarballyate, polydextrose, palatinose, polygalactose, N-oil (tapioca dextrin), microbiologically derived products, nonabsorbable synthetic polymers with properties similar to edible oil, tree-derived products, low-metabolized natural fats and oils, biopolymers, branched polysaccharides and jojoba oil. Many of these are reviewed by Hamre, *J. Food Sci.* 49, 419 (1984).

Alkyl glycoside compositions are known in the art to be useful as detergents, gelling agents, and as food emulsifiers. Baak, U.S. Pat. No. 3,772,269, discloses a method for making alkyl glycosides by reacting monosaccharides with long chain monohydric alcohols in the presence of an acid catalyst.

Gibbons, U.S. Pat. No. 2,759,923, discloses a method for esterification of glucosides with fatty acids in the presence of an alkaline catalyst. Tetraester alkyl glycosides are produced according to the method of Gibbons at temperatures above 200° C. and are suitable for use as drying oils in products such as varnishes.

Gibbons et al., U.S. Pat. No. 2,931,797, discloses mixed methyl glucosideglycerol partial esters produced by alcoholysis of triglycerides with methyl glucoside. These partial esters are suitable for use as nonionic emulsifiers.

Myhre, U.S. Pat. No. 3,597,417, discloses a process for preparing fatty acid esters of sugar glycosides. Myhre first reacts a sugar glycoside with the methyl ester of a short chain acid to produce the sugar glycoside short chain esters. These sugar glycoside short chain esters are then reacted with a long chain fatty acid ester in the presence of an alkali metal alkoxide to produce the sugar glycoside fatty acid ester. Small amounts of these sugar glycoside esters are blended into the shortening component of cake mixes to improve the baking characteristics of the cake mix.

SUMMARY OF THE INVENTION

The present invention provides a process for producing a low calorie food in which the calories derived from fat are reduced. The process consists of substituting, for the normal triglyceride fat ingredients found in foods, a fat substitute comprising an alkyl glycoside fatty acid polyester, the alkyl glycoside fatty acid polyester having at least 4 fatty acid ester groups, wherein each fatty acid has from 4 to 24 carbon atoms, and wherein the alkyl glycoside moiety comprises a saccharide portion and an alkyl portion, as described above. The fatty acids of the fat substitute are selected from unsaturated fatty acids, saturated fatty acids, and mixtures thereof.

To achieve meaningful calorie reduction in the process for producing a low calorie food of the instant invention, greater than 10% and preferably greater than 33% of the fat ingredients of a food should be substituted with the fat substitute alkyl glycoside fatty acid polyester.

Another aspect of the present invention provides a significantly improved process for the manufacture of alkyl glycoside fatty acid polyesters. The process consists of reacting a reducing saccharide with a monohydric, dihydric, trihydric, or tetrahydric alcohol or a hydroxyl-protected derivative thereof as long as at least one free hydroxyl group remains for reaction with the saccharide, thereby forming an alkyl glycoside. The above alcohols may be primary, secondary or tertiary. The alkyl glycoside comprises a saccharide portion and an alkyl portion, wherein the alkyl portion may be unsubstituted or substituted by hydroxyl groups which may be free or protected by standard hydroxyl protecting groups. For example, when the reducing saccharide is reacted with a dihydric alcohol, such as 1,2-dihydroxypropane, one of the two hydroxyl groups on the alcohol can be blocked with, for example, a trityl group or an ester group. If more hydroxyl groups are present on the alcohol reactant, then more protected hydroxyl groups will be present on the alkyl side chain of the intermediate. When stereochemical isomers are possible for the dihydric, trihydric or tetrahydric alcohol reactant, stereochemistry will likewise exist in the alkyl glycoside intermediate. Such isomers may be purified by methods known to those of ordinary skill in the art prior to subsequent reactions, or a mixture of isomers may be utilized in these reactions. The alcohol reactants of the present invention are preferably saturated, but may also be monounsaturated or polyunsaturated. When polyunsaturation is present, both cis- and trans-isomers and mixtures thereof are within the scope of the present invention. After formation of the alkyl glycoside, any protected hydroxyl groups may be deprotected by standard reactions, or subsequent steps may be carried out in the presence of the protected hydroxyl groups.

The hydroxyl groups of these alkyl glycosides (both those on the saccharide and those which have been deprotected on the alkyl moiety of the alkyl glycoside) are then esterified to form a lower acyl ester alkyl glycoside. The lower acyl ester alkyl glycoside is then admixed with a fatty acid lower acyl ester and an alkali metal catalyst thereby forming a reaction mixture which is maintained at a temperature of from about 100° C. to about 125° C. This reaction mixture is maintained at that temperature for a period of up to three hours, preferably from one to three hours. All components of the reaction mixture are thoroughly dried prior to their combination and are kept dry during the period of the reaction by contacting the surface of the reaction mixture with a dry inert gas, such as nitrogen. The fatty acid lower acyl esters and lower acyl alkyl glycosides are combined in molar ratios of from about 4:1 to about 15:1. Either homogeneous or heterogeneous fatty acids lower alkyl esters can be added to their reaction mixture and, in general, the fatty acid portion of the fatty acid lower alkyl ester is a fatty acid having from about 4 to about 24 carbon atoms. The alkyl glycosides of the reaction mixture are the product of the reaction of reducing mono-, di- and trisaccharides with monohydric, dihydric, trihydric, and/or tetrahydric alcohols (or protected derivatives thereof) having from 1 to 24 carbon atoms in the alcohol prior to protection.

DESCRIPTION OF THE INVENTION

In its broadest sense, the process of the present invention for producing alkyl glycoside fatty acid polyesters is a solvent-free, single step synthesis in which the reactants and catalysts are combined prior to heating. Additionally, a vacuum is drawn over the reaction mixture while it is being heated to the reaction temperature and during the time it is maintained at a reaction temperature. Finally, all reagents and implements of the reaction are scrupulously dried to prevent any saponification of any esters present in the reaction mixture.

The alkyl glycoside starting materials for the present invention include alkyl glycosides of mono-, di-, and trisaccharides. These alkyl glycosides can be produced by procedures well known in the art, or purchased from commercial sources. Methods for producing alkyl glycosides from reducing sugars and monohydric alcohols having from 8 to 25 carbons are described by Lew, U.S. Pat. No. 3,772,269, and Klahr et at., U.S. Pat. No. 4,349,669.

A preferred method of forming the alkyl glycoside is a modification of the Koenigs-Knorr procedure. The modification comprises first forming an acylated sugar which is halogenated at the anomeric carbon atom (see Example VII hereinbelow), purifying the acylated halogenated sugar by recrystallization, preparative HPLC, or other bulk purification method, and, thereafter, admixing the purified acylated halogenated sugar with a suitable alcohol (monohydric, dihydric, trihydric or tetrahydric) to form the acylated alkyl glycoside. The latter reaction can be "catalyzed" by silver carbonate, mercury salts or, preferably, a high temperature, high pressure, metal catalyzed bulk procedure. When silver carbonate is used, the precipitated silver halide is recycled to lower cost. Both silver and halide are recoverable. Similarly, when mercury salts are used, they are immobilized on an organic resin so that the reaction product is not contaminated with mercury halide salts. An exemplary method for immobilizing mercury on a resin is to first derivatize the resin with an alkyne, then form the corresponding vinylstannane or vinylboronic esters. The reaction of a vinylstannane with $Hg(OAc)_2$ would yield the corresponding immobilized vinyl-HgOAc derivative. See *J. Org. Chem.* 22, 478 (1957). Similarly, a vinylboronic ester can be reacted with $Hg(OAc)_2$ to yield the corresponding vinyl-HgOAc. See *J. Am. Chem. Soc.* 94, 4371–4373 (1972). The vinyl-HgOAc can be used to pull the halide off the acylated halogenated sugar forming vinyl-Hg-halide and for initiating the SN-1 reaction mechanism with the corresponding alcohol. The sugar may be halogenated with chlorine, bromine or iodine, preferably bromine. The sugar is acylated with a lower (i.e. $C_1$–$C_6$) acyl group, preferably an acetyl group.

Any reducing sugar can be employed in this method. Reducing sugars are defined as those which are capable of reducing the valence of a metal ion in solution (e.g., the Tollins test). Alkyl-providing groups may be alcohols added to the reducing sugar by methods such as the Fischer method or the Koenigs-Knorr method. Alternatively, compounds exhibiting a high alkyl transfer potential such as: dimethylsulfate (or diethylsulfate, etc.), triethylphosphate, dimethylcarbonate, and the like, can be used.

When polyol reactants are used to prepare the alkyl glycoside, the same general methods of synthesis may be utilized as with the monohydric alcohols; however, the hydroxyl moieties not involved in the reaction with the saccharide will generally be protected with conventional hydroxyl-protecting groups.

Examples of suitable reducing saccharides that can be utilized as starting materials are monosaccharides such as fructose, glucose, galactose, mannose, ribulose, rhamnose, xylulose, xylose, ribose, and arabinose. A preferred monosaccharide is glucose. Suitable disaccharides for use in conjunction with the method of the present invention include melibiose, lactose, maltose, and cellobiose. The most preferred disaccharides are lactose and maltose. Trisaccharides utilized in accordance with the method of the present invention include 4'-galactosyl lactose and reducing trisaccharides of galactose, mannose, glucose, and fructose. The most preferred reducing trisaccharide is 4'-galactosyl lactose. By 4'-galactosyl lactose as used herein is meant 0-β-D-galactopyranosyl(1-4)-O-β-D-galactopyranosyl-(1-4)-D-glucose.

Alcohols suitable for forming alkyl glycosides with reducing saccharides include: monohydric, dihydric, trihydric and tetrahydric alkyl, aryl, alkaryl, aralkyl, heteroalkyl, and heteroaryl alcohols. The preferred alcohol starting materials suitable for production of the alkyl glycosides are alkyl alcohols, diols, triols and tetraols having from 1 to 24 carbons. When diols, triols and tetraols (collectively referred to herein as polyols) are used, all hydroxyl groups except one will be blocked or protected by a chemical protecting group to prevent formation of undesirable by-products. Examples of suitable protecting groups are: a trityl group (selective for primary alcohols), an isopropylidene group (for protecting vicinal hydroxyl groups) and a benzylidene group (for protecting [α, γ] hydroxyl groups). Since at least one hydroxyl group must remain available for reaction with the saccharide, it will be understood that, for the purposes of the present invention, isopropylidene and benzylidene groups will only be used in combination with triols and tetraols. It is also possible to protect some of the hydroxyl groups by esterifying them with carboxylic acids (e.g., $C_2$–$C_{20}$, preferably $C_2$–$C_{16}$ straight chain or branched acids). In the case of glycerol, for example, two of the three hydroxyl groups could be esterified to form a diglyceride. Some suitable diglycerides are directly available commercially, such as from Sigma Chemical Co. Of the polyols, the diols and triols are preferred.

One group of preferred alcohols includes straight chain, fully saturated monohydric alcohols having from 1 to 18 carbons. These include, by way of illustration, the following alcohols: methyl, ethyl, n-propyl, n-butyl, n-pentyl, n-octyl, n-decyl, n-dodecyl, n-tetradecyl, n-hexadecyl, and n-octadecyl. Particularly preferred monohydric alcohols are methanol, ethanol and propanol.

Some preferred examples of alcohols having more than one hydroxyl group are the following: glycerol, 1,2-dihydroxypropane, 1,2-dihydroxy($C_4$–$C_{24}$)alkanes, and tetrahydroxy-neopentanes. The preferred tetrahydroxy-neopentane is the one wherein each hydroxyl group is on a different carbon atom. These polyols are readily available either by direct purchase from suppliers, such as Aldrich Chemical Company, or by way of known synthetic procedures reported in the literature.

The alcohol reactants may be straight chain or branched. Examples of branched monohydric alcohols are sec-butanol and tert-butanol. It is also contemplated that other classes of alcohols such as vitamin E, capsaicinoids (e.g., capsaicin and dihydrocapsaicin), and vanillin could also be used to form glycoside intermediates analogous to but structurally distinct from the alkyl glycosides. These compounds can be used in place of the alkyl glycosides in subsequent reactions described hereinbelow.

In order to be usable in accordance with the method of the present invention, hydroxyl groups on the alkyl glycosides (both those on the saccharide and those available for reaction on the alkyl side chain after deprotection) are esterified to form lower acyl ester alkyl glycosides. By lower acyl is meant an acyl group having six or fewer carbon atoms. Preferably, acetyl and propionyl esters are employed. These lower acyl ester alkyl glycosides are formed so that all available hydroxyl groups are converted to esters by conventional methods. An example of a conventional method of esterification that can be employed is the method of Instead, R. P.; Rutenberg, A.; Dauben, W. G.; and Evans, W. L. *J. Am. Chem. Soc.*, 62:3260 (1940). In some cases (e.g., using the Koenigs-Knorr method for forming the alkyl glycoside), the alkyl glycoside will already be acylated (e.g., with acetyl groups) so that further acylation will only be necessary if, after removal of hydroxyl protecting groups from the alkyl moiety of the alkyl glycoside, it is desired to acylate (i.e., esterify) the resulting free hydroxyl groups.

The acylated alkyl glycoside is then purified, e.g., filtered to remove $AgBr_2$ and $AgCO_3$, and the excess alcohol is evaporated to form a crude acylated alkyl glycoside. The acylated alkyl glycoside is then reacted with fatty acid lower alkyl esters to form alkyl glycoside fatty acid polyesters. This interesterification reaction can be conducted by a variety of procedures. For example, interesterification can be catalyzed by sodium metal as set forth in Example 1. The advantage of the sodium catalysis method is that it is a one-step, solvent free, high-yield method. One drawback of the method is the high cost of metallic sodium for commercial scale production. Accordingly, a preferred interesterification procedure is catalyzed by alkali metal carbonate salts (e.g., $Na_2CO_3$) and fatty acid soaps (potassium fatty acid salts). (See for example U.S. Pat. Nos. 3,714,144; 3,558, 597; 3,963,699; 3,996,206 and No. 4,517,360.) Alkali metals, alkali metal carbonate salts, and alkali metal fatty acid soaps are referred to collectively herein as "alkali metal catalysts."

Suitable fatty acid lower alkyl esters produced for use in conjunction with the method of the present invention are made from fatty acids having from 4 to 24 carbon atoms. Examples of fatty acids usable in accordance with the present invention are butyric, caprylic, capric, lauric, myristic, myristoleic, palmitic, palmitoleic, stearic, oleic, ricinoleic, linoleic, linolenic, oleosteric, arachidic, behenic, erucic, arachidonic and lignoceric. Pure fatty acids or naturally occurring fats and oils can serve as a source of the fatty acid components for alkyl glycoside fatty acid polyesters produced in accordance with the present invention. Suitable fats and oils include coconut oil, palm kernel oil, babassu oils, corn oil, soybean oil, safflower seed oil, peanut oil, olive oil, palm oil, sunflower seed oil, sesame seed oil, rapeseed oil, cotton seed oil, cocoa butter, butterfat, lard, beef tallow and menhaden oil. Mixtures of fatty acids derived from soybean, safflower, corn, peanut and cotton seed oils are especially preferred because they contain from about 14 to 18 carbon atoms. In general, it is preferred that the fatty acids range from 14 to 18 carbon atoms because they do not volatilize at the interesterification temperatures.

It has also been discovered that fatty acids derived from naturally occurring fats and oils that have distinct flavor characteristics retain and impart those flavor characteristics to the alkyl glycoside fatty acid polyester fat substitutes produced in accordance with the present invention. For example, fatty acids derived from butterfat, lard, tallow, cocoa butter, sesame oil, olive oil, peanut oil and to a lesser extent coconut oil each have a unique flavor impact. These flavor characteristics have been found to be retained during the interesterification process described below, because the relatively low temperatures of the interesterification process (greater than 95° C.–125° C.) do not result in volatilization of the flavorful fatty acids. This desirable result has been found particularly beneficial for producing alkyl glycoside fatty acid polyesters utilizing fatty acids derived from naturally occurring fats and oils including significant amounts of lower ($C_4$–$C_{12}$) fatty acids, such as butterfat. These lower fatty acids are relatively volatile, and would be distilled off during the derivation of other conventional types of fat substitutes, such as sucrose polyesters. However, the flavor characteristics of butterfat has been found to be retained during the derivation of alkyl glycoside fatty acid polyester fat substitutes with fatty acids from butterfat in accordance with the process set forth herein.

To be suitable for use in accordance with this invention, the fatty acids are converted to lower alkyl fatty acid esters by conventional esterification procedures prior to reacting with a suitable alkyl glycoside lower alkyl ester. Examples of suitable lower alkyl fatty acid esters include, but are not limited to: myristate fatty acid methyl ester (FAME), palmitate FAME, palmitoleate FAME, stearate FAME, oleate FAME, linoleate FAME, myristate fatty acid ethyl ester (FAEE) palmitate FAEE, palmitoleate FAEE, stearate FAEE, oleate FAEE, and linoleate FAEE.

Prior to combining the reactants, both the lower alkyl fatty acid ester and the alkyl glycoside lower alkyl ester are thoroughly dried by conventional procedures, for example, vacuum drying over anhydrous sodium or magnesium sulfate, followed by dry nitrogen purging. The substantially anhydrous lower alkyl fatty acid ester and alkyl glycoside lower alkyl ester are combined in mole ratios of at least 4:1, and preferably from 6:1 to 15:1, depending on the alkyl glycoside lower alkyl ester. To achieve high yields in accordance with the present invention, a catalyst is combined with the reactants prior to heating. Suitable catalysts include the alkali metal catalysts. Sodium and potassium are the most preferred of the alkali metals. Catalysts can be used in amounts up to 5% by weight but are preferably used in amounts of about 2% by weight.

As mentioned above, in order to achieve the high yields possible in accordance with the present invention, all components of the reaction mixture must be combined at room or slightly elevated temperature. It is preferred that the reaction mixture be heated to a reaction temperature of greater than 95° C. gradually, preferably at a heating rate no greater than 3° C. per minute. Preferably reaction temperatures range from 100° C. to 125° C., while the temperature range of 105° C. to 115° C. is most preferred. During the heating and maintenance of the reaction temperature, the area over the reaction vessel is evacuated and flooded with a dry, inert atmosphere. The inert atmosphere can comprise any inert gas, but nitrogen is preferred because of its cost and availability. In order to obtain the yields established in accordance with the present invention, the vacuum pulled over the reaction mixture must be less than 15 torr and, preferably, in the range of from about 0 to 8 torr. Under these conditions, a 95% to 99% yield can be achieved while maintaining the reaction temperature of the reaction mixture for only about two to two and one-half hours. A centrifugal molecular still may be used to achieve rapid and economical purification.

Final products of the present invention wherein the alkyl portion of the alkyl glycoside is substituted with esterified hydroxyl groups may have the advantage over simple alkyl glycosides in that they are not as prone to hydrolysis of the glycosidic linkage. Moreover, ester groups on the alkyl side chain of the alkyl glycoside provide an efficient and economical way to increase hydrophobicity of the overall molecule and decrease absorbability in some cases. When the saccharide moiety is attached via the anomeric carbon atom to a secondary carbon, enhanced stabilization with respect to glycosidases may be conferred.

Alkyl glycoside fatty acid polyesters produced in accordance with the present invention include: methyl glucoside tetraoleate, ethyl glucoside tetraoleate, the ethyl glucoside fatty acid polyester made from peanut oil FAME, methyl glucoside fatty acid polyester made from a 50:50 blend of peanut oil FAME and methyl stearate, ethyl galactoside fatty acid polyester made from peanut oil FAEE, n-octyl glucoside fatty acid polyester made from peanut oil FAEE or FAME, ethyl lactoside fatty acid polyester made from peanut oil FAME, ethyl 4'-galactosyl lactoside fatty acid polyester, isopropyl glucoside fatty acid polyester, glyceryl glucoside fatty acid polyester, 2-esterified isopropyl diol glucoside fatty acid polyester, and the like. By "fatty acid polyester" is preferably meant the tetra, penta, and hexa oleate, stearate, laurate, myristate, peanut oil, and soybean esters.

By alkyl glycoside fatty acid polyesters as used in this invention is meant alkyl glycosides in which four or more of the alkyl glycoside hydroxyl groups on the saccharide moiety have been esterified with a fatty acid. Yields reported for alkyl glycoside fatty acid polyesters in this invention are based on n-1 or more alkyl glycoside hydroxyl groups being esterified with a fatty acid, where n is the maximum number of ester bonds possible (on the saccharide) for a given alkyl glycoside.

Both homogeneous and heterogeneous alkyl glycoside fatty acid polyesters can be produced in accordance with the method of this invention. Examples of preferred homogeneous alkyl glycoside fatty acid polyesters are: methyl glucoside tetraoleate, ethyl glucoside tetraoleate, ethyl galactoside tetrapalmitate, and ethyl lactoside heptastearate. Heterogeneous alkyl glycoside fatty acid polyesters are produced by blending two or more fatty acid lower alkyl fatty acid esters in the reaction mixtures in predetermined ratios. For example, ethyl lactoside heptaacetate, ethyl oleate and ethyl palmitate can be added to the reaction mixture in a ratio of 1:6:4 to produce a heteropolyester of ethyl lactoside. Alternatively, alkyl glycoside lower acyl esters can be reacted with heterogeneous mixtures of fatty acid lower alkyl esters produced from natural oils such as peanut oil to produce heterogeneous alkyl glycoside fatty acid polyesters. An example of such a compound is ethyl 4'-galactosyl lactoside fatty acid polyester made from peanut oil FAME. It is also possible for heterogeneity to be exhibited between the ester groups on the saccharide moiety and the ester groups on the hydroxyl groups available for reaction on the alkyl moiety after deprotection. This heterogeneity may be introduced by standard interesterification or transesterification reactions. For example, the deprotected hydroxyl groups could be acetylated and then interesterified at the same time as the saccharide hydroxyl groups. Alternatively, the hydroxyl groups on the alkyl portion of the alkyl glycoside could remain protected during interesterification on the saccharide group, followed by deprotection and, if desired, final esterification of the deprotected hydroxyl groups (with, e.g., one or more $C_4$–$C_{24}$ saturated or unsaturated fatty acids). Deprotection of protected hydroxyl groups can be accomplished by standard deprotecting reactions depending upon the protecting group used. Generally, for example, treatment of the protected hydroxyl group with a weak acid, hydrogenation, a weak base or a trialkyl borate/boric acid will suffice. Specific conditions can readily be determined by one of ordinary skill in the art.

Alkyl glycoside fatty acid polyesters produced by the above procedures are suitable for use as fat substitute food compositions. Preferred fat substitute food compositions are composed of both nonfat ingredients and fat ingredients wherein from about 5% to about 95% of the total fat ingredients are the alkyl glycoside fatty acid polyesters of the present invention in which the alkyl glycoside is esterified to at least four fatty acids. The alkyl glycoside portion of the alkyl glycoside fatty acid polyester fat substitute food composition is the reaction product of a reducing mono-, di- or trisaccharide with a monohydric, dihydric, trihydric or tetrahydric alcohol having from 2 to 24 carbons in unprotected form. The preferred alkyl glycoside portions are the reaction product of glucose, galactose, lactose or maltose with ethanol, propanol, monohydroxy protected propanediol, or dihydroxy protected glycerol. The dihydroxy protected glycerol is preferably 1,2-isopropylidene glycerol or 1,3-benzylidene glycerol. The fatty acid portion of the alkyl glycoside fatty acid polyester fat substitute food composition is a fatty acid having from 4 to 24 carbons. Preferred fatty acids have from 12 to 18 carbons. These fatty acids may be saturated, unsaturated, straight chain or branched.

It has been discovered that by blending saturated and unsaturated lower alkyl fatty acid esters in the reaction mixture, heterogeneous alkyl glycoside fatty acid polyesters can be produced which do not exhibit undesired anal leakage of the type described below. At least 25% of the lower alkyl fatty acid esters in the reaction mixture must be derived from saturated fatty acids having 12 or more carbons in order to produce a heterogeneous alkyl glycoside fatty acid polyester which does not exhibit anal leakage. It is believed that a substantial portion of the alkyl glycoside molecules contain both saturated and unsaturated fatty acids in the final product. These alkyl glycoside fatty acid polyesters are to be distinguished from the mixed high melting and low melting point alkyl glycoside fatty acid polyester compounds described below.

An alternative alkyl glycoside fatty acid polyester composition suitable for use as a fat substitute food composition is a mixture of low melting point and high melting point alkyl glycoside fatty acid polyesters. Examples of preferred fatty acids suitable for producing low melting point alkyl glycoside fatty acid polyester compounds are $C_{14}$ to $C_{18}$ is unsaturated fatty acids. Equivalent low melting point compounds are produced from sources that produce mixtures of saturated and unsaturated fatty acids. Examples of such compounds are ethyl glycoside fatty acid polyesters from peanut oil FAME. By low melting point alkyl glycoside fatty acid polyester as used herein is meant those alkyl glycoside fatty acid polyesters which are liquid at room temperature.

Preferred high melting point alkyl glycoside fatty acid polyester compounds of the present invention are composed of fatty acid esters in which the fatty acid moiety is a saturated fatty acid having from 12 to 18 carbons. Examples of preferred high melting point alkyl glycoside fatty acid polyester compounds are: methyl glucoside tetralaurate, ethyl glucoside tetramyfistate, ethyl glucoside tetrapalmitate, ethyl galactoside tetrapalmitate and ethyl glucoside tetrastearate. By high melting point alkyl glycoside fatty acid polyester as used herein is meant those alkyl glycoside fatty acid polyesters which are solid at temperatures above 37° C.

It has been discovered that alkyl glycoside fatty acid polyesters that have a melting point of about 37° C. or higher can act as anti-anal leakage agents (AAL) of the type described by Jandacek, U.S. Pat. No. 4,005,195 and Robbins et al., U.S. Pat. No. 4,461,782. Accordingly, an effective amount of these glycoside AAL agents can be blended with low melting point alkyl glycoside fatty acid polyesters to produce fat substitute food compositions which do not exhibit the undesirable anal leakage side effect observed when homogeneous low melting point glycoside fatty acid polyesters are used as low calorie fat substitutes alone. Suitable alkyl glycoside fatty acid polyester AAL agents are produced by interesterification of lower acyl ester glycosides with lower alkyl fatty acid esters wherein the fatty acid moiety of the lower alkyl fatty acid ester is a saturated fatty acid having from 14 to 18 carbon atoms. Preferred saturated fatty acids are palmitic and stearic acid. Equivalent glycoside AAL agents are produced by the interesterification of lower alkyl fatty acid esters with blends of lower alkyl fatty acid esters wherein the fatty acid moiety is predominantly saturated with lesser amounts of unsaturated fatty acids. The critical property of the resultant glycoside AAL agent being only that it have a melting point higher than 37°.

Examples of low calorie fat substitute food compositions of the present invention which do not exhibit the undesired anal leakage side effects are provided in Table I below.

TABLE I

| Low Melting Point Alkyl Glycoside Fatty Acid Polyester Agent | High Melting Alkyl Glycoside Fatty Acid Polyester AAL |
| --- | --- |
| Ethyl glucoside tetraoleate | Ethyl glucoside tetrapalmitate |

TABLE I-continued

| Low Melting Point Alkyl Glycoside Fatty Acid Polyester Agent | High Melting Alkyl Glycoside Fatty Acid Polyester AAL |
| --- | --- |
| Ethyl galactoside fatty acid polyester of peanut oil FAME | Ethyl glucoside tetrapalmitate |
| Ethyl 4'-galactosyl lactoside fatty acid polyester of peanut oil FAME | Ethyl glucoside tetrapalmitate |
| n-octylglucoside fatty acid polyester of peanut oil FAME | Ethyl galactoside tetrastearate or n-octyl glucoside tetrastearate |
| Ethyl glucoside fatty acid polyester of peanut oil FAME | Ethyl galactoside tetrastearate |
| Ethyl lactoside fatty acid polyester of peanut oil FAME | Ethyl lactoside octastearate |

The amount of AAL agent to be blended with the low melting point glycoside fatty acid polyester is known to those skilled in the art and depends upon the amount of low calorie fat substitute composition consumed. It is preferred that from about 5% to about 50% of the fat ingredients in the fat substitute food composition consist essentially of a high melting point alkyl glycoside fatty acid polyester.

It has also been found that glyceryl glycoside polyesters produced in accordance with the present invention do not have an associated anal leakage effect, even when used at a level of 100% of a fat substitute, without an additional AAL agent. Further, glyceryl glycoside polyesters can be used as AALs in conjunction with other nondigestible fat substitutes.

Particularly, it is thought that the fatty acids esterified to the glyceryl portion of glyceryl glucoside hexa ($C_4$–$C_{24}$ fatty acid) ester are hydrolyzable in vivo, and thus would be delivered to the body after consumption. Also, the remaining alkyl glucoside tetraester will possess emulsifying properties in the gut, and thus will reduce the need for an AAL agent. Other groups attached to the glycoside in place of the alkyl group, such as Vitamin E, might also be hydrolyzed off in vivo and thus delivered to the body.

Process for Producing Low Calorie Foods

Low calorie foods are produced in accordance with the present invention by preparing foods according to art standard recipes and procedures, with the substitution of the alkyl glycoside fatty acid polyester fat substitute for at least a portion of the triglyceride fat ingredients normally found in foods. The instant fat substitute is particularly well-suited for replacing the triglyceride fat ingredients in foods containing "visible fats" such as: shortenings, margarines, butter, salad and cooking oils, mayonnaise, salad dressing, confectioners' coatings, and the like. The instant fat substitute is also suitable for replacing the fat ingredients in foods containing "invisible fats", such as oilseeds, nuts, dairy products, and animal products. By the term "visible fat", as used herein, it is meant fats and oils that have been isolated from animal tissues, oilseeds, or vegetable sources and are used or added to produce the food products described above. The term "invisible fat" is used herein to mean fats and oils that have not been or are not isolated from animal or vegetable sources, and are consumed along with the protein and carbohydrate constituents of these sources as they are naturally constituted. Fat ingredients normally found in foods containing either "visible fats" or "invisible fats" are predominantly triglycerides, with minor amounts of mono- and diglycerides, free fatty acids, phosphatides, sterols, fatty alcohols, tocopherols, carotenoids, and certain vitamins.

To prepare a low calorie food from one having "invisible fat" ingredients generally requires the removal of a portion of the "invisible fat" ingredients, followed by addition of an equal, greater or lesser amount of the alkyl glycoside fatty acid polyester fat substitute. By way of example, a low calorie spreadable peanut product that is nutritionally equivalent to peanut butter (i.e., has the same protein quantity and quality), but without as many calories, can be prepared by removing a portion of the peanut oil from the peanut butter and replacing it with an alkyl glycoside fatty acid polyester (preferably prepared from peanut oil FAME). Removing the endogenous peanut oil can be achieved by merely decanting the oil from unstabilized peanut butter, or by simple oil extraction.

Foods having "visible fat" ingredients are ones in which a triglyceride fat or oil is usually added to other ingredients to prepare the food product. To prepare a low calorie food from one having "visible fat" ingredients, at least a portion of the added triglyceride fat or oil ingredients are replaced with the alkyl glycoside fatty acid fat substitute of the present invention.

According to the instant invention a low calorie food, containing nonfat ingredients and fat ingredients, either "visible" or "invisible", is prepared by substituting for the fat ingredients a fat substitute comprising an alkyl glycoside fatty acid polyester, as defined above. By the term substituting, as used herein, it is meant either simply replacing exogenously added triglyceride fat ingredients, or removing endogenous fat ingredients, from food, followed by addition of an equal, greater or lesser amount of the alkyl glycoside fatty acid polyester.

The fatty acid ester moiety of the alkyl glycoside fatty acid polyester fat substitute may be selected from among saturated fatty acids, unsaturated fatty acids and mixtures thereof. However, it is preferred, for most uses, that the fatty acid ester groups be selected from the group consisting of unsaturated fatty acids, and mixtures of saturated and unsaturated fatty acids having from 4 to 24 carbon atoms. The terms saturated and unsaturated fatty acids are used herein in their normal sense, regardless of how they are formed (i.e., hydrogenation or partial hydrogenation). Included in the term unsaturated is monounsaturated (mono-enoic) and polyunsaturated (poly-enoic), as well as specific positional isomers.

In order to achieve highly desirable organoleptic properties, it is most preferred that the composition of the fatty acid in the alkyl glycoside fatty acid polyester be the same or equivalent to the composition of fatty acids in the triglycerides they replace. By way of example, the most preferred fatty acid ester groups in an alkyl glycoside fatty acid polyester used to replace peanut oil in a low calorie spreadable peanut product would be peanut oil fatty acid ester groups. Similarly, a low calorie Italian salad dressing normally containing safflower oil as the fat ingredient would be prepared by replacing at least a portion of the safflower oil with an alkyl glycoside fatty acid polyester made from safflower oil FAME. Tables describing the composition of fatty acids in typical triglyceride vegetable oils and animal fats are readily available (see for example Table VII p. 21 in *Food Fats and Oils*, Institute of Shortening and Edible Oils, Inc., 1750 New York Avenue N.W., Washington, D.C.).

The amount of alkyl glycoside fatty acid polyester to be substituted for the fat ingredients in a low calorie food product depends on the application. In most cases, greater than 10% of the fat ingredients are replaced with the alkyl glycoside fatty acid polyester to achieve meaningful calorie reduction. Up to 100% of the fat ingredients of a food can be substituted with the alkyl glycoside fatty acid polyester of the present invention. However, it is recognized that fat ingredients provide many essential nutrients in human and animal diets. For example, fat ingredients in foods provide fatty acids, which are precursors of the prostaglandins as well as being carriers for fat soluble vitamins. It is therefore preferred that less than 100% of the fat ingredients be replaced by the fat substitute of the instant invention in any one food product. Accordingly, it is preferred that from 25%–85% of the fat ingredients in a food be replaced with an alkyl glycoside fatty acid polyester fat substitute, while it is most preferred that from 33%–75% be replaced with this fat substitute.

The alkyl glycoside fatty acid polyester fat substitute may be composed of a single homogeneous (saturated or unsaturated) or heterogeneous (saturated or unsaturated) alkyl glycoside fatty acid molecular species, or may be a mixture of two or more molecular species. By way of illustration, a fat substitute composed of a mixture of alkyl glycoside fatty acid polyesters is prepared by mixing two or more alkyl glycoside fatty acid polyesters in which the fatty acid moieties are selected from among: homogeneous saturated, homogeneous unsaturated, heterogeneous saturated, heterogeneous unsaturated, and a mixture of heterogeneous saturated and unsaturated. For example, a low calorie food prepared by substituting for the fat ingredients a mixture of alkyl glycoside fatty acid polyesters, in which the fatty acids are unsaturated fatty acids, would be a mixture of methyl glucoside tetraoleate and ethyl galactoside tetrapalmitate, or a mixture of methyl glucoside dioleate-dilinoleate and methyl glucoside dicaproleatedilauroleate. Similarly, an example of a mixture of alkyl glycoside fatty acid polyesters, in which the fatty acids are selected from saturated and unsaturated fatty acids, would be methyl glucoside tetrapalmitate and ethyl galactoside tetraoleate, or methyl glucoside polyester, prepared from corn oil FAME, and ethyl galactoside polyester prepared from rapeseed oil.

Optionally, the fat substitute may include an anti-anal leakage agent (AAL) of the type described by Jandacek, U.S. Pat. No. 4,005,195, herein incorporated by reference. Exemplary anti-anal leakage agents include fatty acids having melting points above 37° C. and sources thereof: i.e., mono-, di- and triglycerides; non-reducing di- and trisaccharide polyesters having $C_{10}$–$C_{22}$ saturated fatty acid ester groups; and alkyl glycoside fatty acid polyesters having melt points above 37° C. Also, optionally, the fat substitute of this invention may include essential fat nutrients, (e.g., 20-carbon, polyunsaturated fatty acids, especially arachidonic acid) and fat soluble vitamins.

In most cases, it is unnecessary to add anti-anal leakage agents to the fat substitute of the instant invention. This is especially the case when the diet is a normal one and includes foods containing "invisible fats", such as dairy products, eggs, meat, poultry, fish, fruits, vegetables, legumes, nuts, soy, grains and the like. "Invisible fats" found in animal tissues, oilseeds, or vegetable sources are consumed as a normal part of the diet, and are known to comprise 57% of the fat available for consumption in the normal U.S. diet. A portion of these "invisible fats" are triglyceride sources of fatty acids, having melting points above 37° C. (i.e., AAL agents), and therefore it is unnecessary to include any other AAL agents in the fat substitute. Accordingly, alkyl glycoside fatty acid polyesters containing all unsaturated fatty acid ester groups are especially useful as fat substitutes in replacing triglyceride fats and oils in food products containing "visible fats".

The alkyl glycoside fatty acid polyester fat substitutes of the present invention are also useful for cooking foods (i.e., frying, basting, coating, etc.). In this respect, use of the instant fat substitutes does not depart from normal cooking procedures (see for example *Joy of Cooking* by Irma Rombauer and Marion Rombauer-Becker), except that nominal triglyceride fats and oils are replaced in part or in total with an alkyl glycoside fatty acid polyester. By way of illustration, a low caloried fried food product is produced by heating a fat substitute comprising an alkyl glycoside fatty acid polyester as defined above, and thereafter contacting a food with the heated fat substitute for a time effective to produce a low caloried fried food product. Similarly, low calorie foods may be produced by simply contacting a food with the alkyl glycoside of the instant invention, as for example in basting foods. One of ordinary skill will appreciate the many other uses of the instant fat substitute in preparing low calorie and low fat foods.

The following examples are intended to be illustrative of the present invention and to teach one of ordinary skill how to make and use the invention. These examples are not intended in any way to limit the invention or otherwise limit the protection afforded by Letters Patent hereon.

PREPARATION OF ALKYLGLYCOSIDE POLYESTERS

EXAMPLE I

Ethyl glucoside tetraacetate

In a 1000 ml three-necked flask equipped with an efficient stirrer and a thermometer, 400 ml acetic anhydride is cooled in an ice and $H_2O$ mixture. 20 mls of conc. $H_2SO_4$ is added to the mixture dropwise. The solution is cooled to below 20° C. and 100.0 g of anhydrous D-glucose is added to the stirred mixture, over a ½ hour period. The reaction temperature is maintained between 30° C. and 40° C. Red phosphorus (30 g) is added after cooling the mixture to 20° C., followed by the addition of 180 g bromine (58 ml) at a rate sufficient to keep the reaction temperature below 20° C. Water (3.6 ml) is added dropwise to the continuously stirred and cooled mixture over about a ½ hour period to prevent the temperature from rising over 20° C. The reaction mixture is kept at room temperature for 2 hours. Methylene chloride (300 ml) is then added, and the mixture is filtered through fine glass wool. The reaction flask and filter funnel are washed with 50 ml $Ch_2Cl_2$. The filtrate is poured into water (near 0° C.) contained in a separatory funnel. After washing, the $CH_2Cl_2$ layer is drawn off into another separatory funnel into 0° C. water. The operation is repeated by adding 50 ml $CH_2Cl_2$ to the original aqueous mixture and combining the $CH_2Cl_2$ extracts. After vigorous shaking, the $CH_2Cl_2$ layer is poured into 50 mls of a stirred saturated aqueous solution of sodium hydrogen carbonate pH 6.0. The $CH_2Cl_2$ layer is then dried with $NaSO_4$, and the mixture is filtered. The product, acetyl bromoglucose, is recrystallized twice from diethyl ether. The crystalline mass is then admixed with ethanol in the presence of an equimolar amount of $Ag_2CO_3$ and maintained at a temperature of 30°–40° C. for 16 hours, with vigorous mixing in the dark. The crude ethyl glucoside tetraacetate is crystallized twice from ethanol as described above, to produce substantially pure ethyl glucoside tetraacetate.

EXAMPLE II

Ethyl galactoside tetraacetate

D-galactose is substituted for D-glucose in the reaction mixture described in Example 1. Ethyl galactoside tetraacetate is recrystallized from methylene chloride.

EXAMPLE III

4'-galactosyl lactose

4'-galactose lactose is prepared by adding 1200 g lactose to a 10 liter jar fermentor containing 6 liters of a *Cryptococcus laurentii* broth containing neopepetone (10 g/l) and dextrose (20 g/l) at pH 5.6. The broth containing lactose is incubated at 25°–30° C. for 6 hrs, after which it is centrifuged to remove the microorganisms. The eluate is chromatographed on an activated carbon column, concentrated, filtered and the 4'-galactosyl lactose is crystallized from ethanol.

EXAMPLE IV

Ethyl 4'-galactosyl lactoside decaacetate 30 g of 4'-galactosyl lactose produced as described in Example III is substituted for the D-glucose in the reaction mixture described in Example 1. Crude ethyl 4'-galactosyl lactose decaacetate is recrystallized from $CH_2$ $Cl_2$ as described above.

EXAMPLE V

Ethyl 4'-galactosyl lactose polyoleate

Methyl oleate (51 g, 0.1720 mole) is placed in a three-necked, round-bottomed flask equipped with a magnetic stirrer, stopcocks, a vacuum take-off line leading to a liquid nitrogen cold trap, manometer, two condensers, thermometers, a vacuum pump and purged with dry $N_2$ gas for 30 min. Ethyl 4'-galactosyl lactose decaacetate (15 g, 0.0155 mole) is added and the $N_2$ purging is continued for an additional 15 min. The mole ratio of methyl oleate to ethyl 4'-galactosyl lactose decaacetate is 11: 1. Sodium metal (2% of the reactants by weight, 1.3 g) is added. Heating is started with continuous stirring under dry nitrogen atmosphere. The reaction mixture is heated to 110° C. to 115° C. and pressure is maintained at 0 to 8 torr. Synthesis of alkyl glycoside polyesters requires constant dispersion of liquid sodium, liquid ethyl 4'-galactosyl lactose decaacetate and liquid fatty acid methyl esters for optimal interesterification under $N_2$ gas. Interesterification is assumed to begin when catalytic sodium metal and ethyl 4'-galactosyl lactose decaacetate melts and the reaction mixture becomes homogeneous. Interesterification is continued under constant conditions for two and one-half hours. Volatile methyl acetate is condensed on a liquid nitrogen Dewer column to drive the reaction towards ethyl 4'-galactose lactose esterification. Ethyl 4' galactose lactose polyoleate is purified by a modification of the method of Hamm, *J. Food Sci.* 49:419 (1984). The crude ethyl 4'-galactose lactose polyoleate reaction mixture is neutralized with sufficient acid, dissolved in hexane, stirred and bleached with activated charcoal. The reaction mixture is then filtered with Whatman No. 4 filter paper to remove charcoal particles, and the filtrate is washed with 6×400 ml aliquots of methanol allowing enough time for separation. The more dense methanol insoluble layer containing ethyl 4'-galactosyl lactose polyoleate is separated, dried over anhydrous sodium sulfate and filtered with Whatman No. 4 filter paper. Methanol and hexane are then evaporated from ethyl 4'-galactosyl lactose polyoleate. The color of the polyester is golden yellow, similar to corn oil.

EXAMPLE VI

Ethyl 4'-galactosyl lactose polyester from soybean oil FAME

The procedure of Example V is repeated substituting 63.26 g of soybean oil FAME for methyl oleate. The average molecular weight of soybean FAME is assumed to be about 278.01. Ethyl 4'-galactosyl lactose decaacetate (20 g, 0.0207 mole) is added to the soybean FAME. An ethyl 4'-galactosyl lactose polyester of soybean oil is produced.

EXAMPLE VII

Ethyl 4'-galactosyl lactose polyester from safflower oil FAME and methyl stearate The procedure of Example V is repeated by combining methyl stearate (8.04 g), safflower oil FAME (32.16 g), ethyl 4'-galactosyl lactose decaacetate (12.00 g) and 2% by weight Na (1-04 g). An ethyl 4'-galactosyl lactose polyester of 80:20 (w/w) blend of safflower oil FAME and methyl stearate is produced.

EXAMPLE VIII

Ethyl lactoside polyester from safflower oil FAME and methyl stearate

Substantially anhydrous methyl stearate (4.34 g), safflower oil fatty acid methyl ester (FAME) (39.06 g), and ethyl lactoside heptaacetate (12.5 g) are mixed with 2% by weight Na (1.12 g), based on the weight of the reactants. Interesterification is carried out under dry $N_2$ atmosphere by first gradually heating the reaction mixture to a temperature in the range of 105° C. to 110° C. and maintaining that temperature for two hours. The pressure over the reaction vessel is maintained at 0 to 5 torr. The mole ratio of the fatty acid methyl esters to ethyl lactoside heptaacetate is 7:1. An ethyl lactoside fatty acid polyester of 90:10 (w/w) blend of safflower oil FAME and methyl stearate is produced. The crude methyl lactoside fatty acid polyester is purified as described in Example V.

The foregoing procedure is repeated, except the safflower oil FAME and methyl stearate blend is replaced by an equivalent amount of safflower oil FAME alone. Ethyl lactoside fatty acid polyester of safflower oil FAME is produced.

EXAMPLE IX

Ethyl lactoside polyester from soybean oil FAME

Substantially anhydrous soybean oil FAME (0.2947 mole) and ethyl lactoside heptaacetate (0.0368 mole) are mixed with 2% by weight sodium metal (2.1 g). The mole ratio of soybean oil FAME to ethyl lactoside heptaacetate is 7:1. Interesterification is performed under dry $N_2$ atmosphere at 115° C. to 118° C. for three hours. The pressure is maintained at 0 to 5 torr. Purification of the crude ethyl lactoside polyester is performed essentially as described in Example V.

EXAMPLE X

Ethyl maltoside polyoleate

Substantially anhydrous methyl oleate 97% pure (69.9 g, 0.2358 mole) and ethyl maltoside heptaacetate (20 g, 0.0294 mole) and 2% Na (1.8 g) are mixed. interesterification is carried out at 105° C. to 110° C. for two and one-half hours under the conditions set forth in Example V. The final mole ratio of methyl oleate to ethyl maltoside heptaacetate is 7:1.

EXAMPLE XI

Ethyl lactoside, glucoside and galactoside polyoleate 20 g of D-lactose is substituted for the D-glucose described in Example I. Interesterification of the ethyl lactoside heptaacetate with methyl oleate is conducted according to the method of Example V yielding ethyl lactoside polyoleate. Similarly, interesterification of ethyl glycoside tetraacetate and ethyl galactoside tetraacetate (see Example II) with methyl oleate according to the method of Example V yields ethyl glucoside tetraoleate and ethyl galactoside tetraoleate respectively.

EXAMPLE XII

For each equivalent of hydroxy functions on an alkyl glycoside, two equivalents of acetyl chloride are placed in a stirred reaction vessel. If the alkyl glycoside is in an alcohol solvent, the hydroxy functions of the solvent must also be exceeded by the acetyl chloride. An inert gas is continuously flushed through the apparatus through a back flush trap and into a water trap containing NaOH. The alkyl glycoside is added slowly to the acetyl chloride while maintaining the reaction temperature between 30° C. and 40° C. When all the glycoside has been added, stirring is continued for one hour. The acetyl chloride is then completely consumed by addition of an excess of 1-butanol. The reaction solution now consists of the acyl alkyl glycoside, the acetate ester of the solvent alcohol (i.e., ethyl acetate), butyl acetate and butanol. The hydrochloric acid produced by the reaction

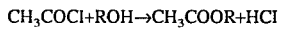

$$CH_3COCl + ROH \rightarrow CH_3COOR + HCl$$

will not volatilize off completely due to the pka's of the esters, so the solution is neutralized with cautious addition of a saturated aqueous solution of sodium bicarbonate ($NaHCO_3$) until all gas evolution ceases. The aqueous phase is drained from the bottom of the vessel by stopcock or pipette and the solution washed with water one or two times. The butyl acetate/butanol solvent assures that the acyl alkyl glycoside remains separate from the water.

The final traces of water are removed by attaching a side-arm receiver and condenser to the reaction flask and heating the solution to a vigorous boil until no further accumulation of water is observed in the receiver.

The side-arm receiver is removed and a high-vacuum distillation of the solvents leaves only acyl alkyl glycoside in the reaction vessel. Fatty acid methyl ester (FAME) is introduced at a ratio appropriate for interesterification to the alkyl glycoside, and high vacuum distillation is again applied to draw off any residual solvents in the FAME. Finally, sodium metal catalyst is added at 2% of the total amount, then high-vacuum distillation is used to remove methyl acetate produced upon heating above 95° C., driving the interesterification reaction to completion. The final product is washed out of the reaction vessel onto a silica gel chromatography column and eluted using a mobile phase of 9:1 hexane:ethyl ether. Residual FAME elute first, followed by alkyl glycoside fatty acid polyester (AGFAP) which is fully esterified. Any alkyl glycoside not fully esterified will elute very slowly or not at all under these conditions, so the critical cut is between FAME and AGFAP.

EXAMPLE XIII 2,2-Dimethyl-1,3-dioxolane-4-methanol, also known as 1,2-isopropylidene glycerol, is substituted for ethanol in the final step of Example I. 1-0-4(2,2-dimethyl-1,3-dioxotane) glucoside tetraacetate is recrystallized from $CH_2Cl_2$.

EXAMPLE XIV

The product of Example XIII is substituted for ethyl 4'-galactosyl lactose in Example I yielding 1-0-4(2,2-dimethyl-1,3-dioxolane) glucoside tetraoleate.

The isopropylidene protecting group is replaced with dimethyl borate by heating in the presence of boric acid and trimethyl borate, keeping the temperature below 100° C. Finally, water washing of the reaction mixture removes dimethyl borate, yielding 1-0-3(1,2-hydroxy propane) glucoside tetraoleate. See Mattson et al., *J. Lipid Research*, July 62, Vol. 3, p. 282.

The free hydroxyl groups of this compound are then esterified selectively by slow addition to the acid chloride of the desired fatty acid, maintaining a reaction temperature between 30°–40° C. or just above the melting point of higher melting fatty acid chlorides (e.g., stearic acid chloride).

The final product is purified as in Example XII or by centrifugal molecular distillation, yielding glyceryl glucoside hexaester having well-defined fatty acids esterified to the glyceryl moiety.

EXAMPLE XV

The product of Example XII is deprotected as in Example XIV before interesterification, then is esterified as the alkyl glycoside in Example XII, yielding glyceryl glucoside hexa($C_{4-24}$ fatty acid) ester.

EXAMPLE XVI

Methyl glucoside polyester of butterfat and myristate fatty acids

Methanol is substituted for the ethanol in Example 1, yielding methyl glucoside tetraacetate. The methyl glucoside tetraacetate was interesterified with fatty acids derived from butterfat and ethyl myristate, in a molar ratio of 75:25, according to the method of Example V yields a plastic methyl glucoside polyester with a pronounced butterfat flavor.

DEEP FAT FRYING

EXAMPLE XVII

Low calorie potato chips are produced by frying thin potato slices in ethyl lactoside polyoleate. For each chip a 5 g aliquot of ethyl lactoside polyoleate is poured into a small glass cooking vessel and heated to approximately 360° F. Small potato slices having a thickness of 2 to 3 mm and a diameter of 2 to 3 cm are added to the oil and fried until done.

EXAMPLE XVIII

Low calorie potato chips are produced by the method of Example XVII by substituting ethyl glucoside tetraester for the ethyl lactoside polyoleate. The ethyl glucoside tetraester is produced by reacting ethyl glucoside tetraacetate, ethyl myristate and ethyl oleate in a ratio of 1:2:6 according to the method of Example V.

EXAMPLE XIX

Low calorie potato chips are produced by frying thin potato slices in ethyl glucoside polyester frying oil. For each potato chip, a 4 g aliquot of ethyl glucoside tetraoleate is combined with a 1 g aliquot of ethyl glucoside tetrapalmitate and the resulting mixture is poured into a small glass cooking vessel and heated to approximately 360° F. Small potato slices, having a thickness of 2 to 3 mm and a diameter of 2 to 3 cm are added to the oil and fried until done. Low calorie potato chips produced in this way have satisfactory texture.

EXAMPLE XX

The procedure described in Example XIX is employed to produce low calorie potato chips by substituting the same quantity of ethyl galactoside fatty acid polyester of peanut oil FAME for ethyl glucoside tetraoleate in the frying oil.

EXAMPLE XXI

The procedure described in Example XIX is employed to produce low calorie potato chips by substituting the same quantity of ethyl lactoside heptastearate for ethyl glucoside tetrapalmitate in the frying oil. These low calorie potato chips have satisfactory texture and flavor.

EXAMPLE XXII

The procedure described in Example XIX is employed to produce low calorie potato chips by substituting the same quantity of sucrose octapalmitate for the ethyl glucoside tetrapalmitate.

EXAMPLE XXIII

The procedure described in Example XIX is employed to produce low calorie potato chips by substituting the same quantity of tripalmitin for the ethyl glucoside tetrapalmitate.

EXAMPLE XXIV

The procedure described in Example XIX is employed to produce satisfactory low calorie potato chips by substituting the same quantity of ethyl glucoside fatty acid polyester of peanut oil FAEE for ethyl glucoside tetraoleate in the frying oil.

EXAMPLE XXV

The procedure described in Example XIX is employed to produce satisfactory low calorie potato chips by substituting the same quantity of ethyl 4'-galactosyl lactoside fatty acid polyester for ethyl glucoside tetraoleate in the frying oil.

SPOONABLE WHITE SALAD DRESSING

EXAMPLE XXVI

A low calorie spoonable white salad dressing is prepared by replacing the oil in a typical recipe of this type with ethyl 4'-galactosyl lactose fatty acid polyester prepared from safflower oil FAEE. Mixing the ingredients in the proportions below produced a salad dressing with satisfactory consistency and taste.

| Ingredient | Percent by Weight |
| --- | --- |
| Ethyl 4'-galactosyl lactose fatty acid polyester | 30.0 |
| Starch paste | 60.0 |
| starch | |
| sugar | |
| salt | |
| vinegar | |
| water | |
| Egg yolk | 5.0 |
| Water | 3.9 |
| Vinegar | 1.0 |
| Gum | 0.1 |
| | 100.0 |

Similar results are obtained when the 30% Ethyl 4'-galactosyl lactose fatty acid polyester is substituted with 4% ethyl glucoside tetraoleate and 26% safflower oil.

EXAMPLE XXVII

A low calorie spoonable white salad dressing is prepared by replacing the oil in a typical recipe of this type with ethyl glucoside polyesters. Mixing the ingredients in the proportions below produced a salad dressing with satisfactory consistency and taste.

| Ingredient | Percent by Weight |
| --- | --- |
| Ethyl glucoside tetraoleate | 20.0 |
| Ethyl glucoside tetrapalmitate | 10.0 |
| Starch paste | 60.0 |
| starch | |
| sugar | |
| salt | |
| vinegar | |
| water | |
| Egg yolk | 5.0 |
| Water | 3.9 |
| Vinegar | 1.0 |
| Gum | 0.1 |
| | 100.0 |

Similar results are obtained when sucrose octapalmitate is substituted for the ethyl glucoside tetrapalmitate.

EXAMPLE XXVIII

The ingredients in Example XXVII are employed to produce a satisfactory low calorie spoonable white salad dressing by substituting the same quantity ethyl glucoside fatty acid polyester of peanut oil FAME for ethyl glucoside tetraoleate in the oil.

EXAMPLE XXIX

The ingredients in Example XXVII are employed to produce a satisfactory low calorie spoonable white salad dressing by substituting the same quantity of ethyl galactoside tetrastearate for ethyl glucoside tetrapalmitate in the oil.

EXAMPLE XXX

The ingredients in Example XXVII are employed to produce a satisfactory low calorie spoonable white salad dressing by substituting the same quantity of ethyl 4'-galactosyl lactoside fatty acid polyester for ethyl glucoside tetraoleate in the oil.

ITALIAN SALAD DRESSING

EXAMPLE XXXI

A low calorie Italian salad dressing is prepared by replacing the oil found in typical recipes of this type with ethyl 4'-galactosyl lactose fatty acid polyester prepared from safflower FAEE as described in Example VII.

| Ingredient | Percent by Weight |
| --- | --- |
| Ethyl 4'-galactosyl lactose fatty acid polyester | 40.00 |
| Water | 35.45 |
| Lemon juice | 5.80 |
| Vinegar (120 grain) | 13.00 |
| Salt | 3.50 |
| Starch | 0.80 |
| Garlic | 2.00 |
| Onion and garlic | 1.00 |
| Other spices | 0.25 |
| | 100.00 |

Similar results are obtained by substituting 20% safflower oil, 10% ethyl glucoside tetraoleate, and 10% ethyl glucoside tetramyristate for the ethyl 4'-galactosyl lactose polyester.

EXAMPLE XXXII

Low calorie salad dressing is produced by substituting the same percent by weight of ethyl lactoside fatty acid polyester prepared as described in Example VII for the ethyl 4'-galactosyl lactose fatty acid polyester in the salad dressing recipe of Example XXXI.

EXAMPLE XXXIII

A low calorie Italian salad dressing is prepared by substituting the triglyceride oil found in typical recipes of this type with ethyl lactoside polyester prepared from safflower FAME as described in Example VIII, and the glycoside AAL agent ethyl lactoside heptastearate.

| Ingredient | Percent by Weight |
| --- | --- |
| Ethyl lactoside from safflower FAME | 30.00 |
| Ethyl lactoside heptastearate | 10.00 |
| Water | 35.45 |
| Lemon juice | 5.80 |
| Vinegar (120 grain) | 13.00 |
| Salt | 3.50 |
| Starch | 0.80 |
| Garlic | 2.00 |
| Onion and garlic | 1.00 |
| Other spices | 0.25 |
| | 100.00 |

EXAMPLE XXXIV

Low calorie salad dressing is produced by substituting the same percent by weight of ethyl galactoside tetraoleate prepared as described above for the ethyl glucoside tetraoleate in the salad dressing recipe of Example XXVIII.

All of the alkyl glycoside fatty acid polyesters produced in accordance with the present invention are usable as substitutes for naturally occurring fats and oils. The process and the novel products produced have been described in conjunction with preferred embodiments. One of ordinary skill, after reviewing the foregoing specification, will be able to make various changes, substitutions of equivalents, and other alterations without departing from the broad concepts disclosed herein. It is therefore intended that protection afforded by Letters Patent hereon be limited only by the definition contained in the appended claims and equivalents thereof.

While the preferred embodiment of the invention has been described, other modifications may be made thereto and other embodiments may be devised within the spirit of the invention and scope of the appended claims.

The embodiments of the invention in which an exclusive property or privilege is claimed are defined as follows:

1. A process for producing an alkyl glycoside fatty acid polyester comprising the steps of:

reacting a lower acylated reducing saccharide halogenated at the anomeric carbon with a monohydric, dihydric, trihydric or tetrahydric alcohol having at least one free hydroxyl group, the remaining hydroxyl groups being protected wkh hydroxyl protecting groups, thereby forming a lower acyl ester alkyl glycoside;

removing any protecting groups on the alkyl moiety of the lower acyl ester alkyl glycoside;

admixing the lower acyl ester alkyl glycoside, a fatty acid lower alkyl ester, and an alkali metal catalyst to form a reaction mixture;

heating said reaction mixture to a reaction temperature in the range of from 100° to 125° C. and maintaining the reaction temperature for a period of from one to three hours;

while maintaining the reaction temperature, drawing a vacuum of from about 0 to 10 torr over the reaction mixture to obtain a yield of at least 95% of an alkyl glycoside fatty acid polyester in the reaction mixture; and recovering an alkyl glycoside fatty acid polyester from the reaction mixture.

2. The process of claim 1, wherein said catalyst comprises potassium metal or sodium metal.

3. The process of claim 1, wherein said catalyst comprises a combination of an alkali metal carbonate and an alkali metal salt of a $C_4$–$C_{24}$ fatty acid.

4. The process of claim 1, comprising the further step of contacting the surface of the reaction mixture with a dry inert gas while said reaction mixture is maintained at the reaction temperature.

5. The process of claim 1, wherein the mixture is heated to the reaction temperature at a rate less than 3° C. per minute.

6. The process of claim 1, wherein the fatty acid lower alkyl esters and lower acyl ester alkyl glycoside are combined in molar ratios of from 4:1 to 15:1.

7. The process of claim 1, wherein the fatty acid lower alkyl esters and lower acyl ester alkyl glycoside are thoroughly dried.

8. The process of claim 1, wherein the lower alkyl groups comprise methyl or ethyl, and the lower acyl groups comprise acetyl or propionyl.

9. The process of claim 1, wherein the fatty acid moiety of the fatty acid lower alkyl ester comprises fatty acids having from 4 to 24 carbon atoms.

10. The process of claim 9, wherein at least some of the fatty acid moieties of at least a portion of the fatty acid lower alkyl ester comprises fatty acids having from 4 to 12 carbon atoms.

11. The process of claim 10, wherein at least some of the fatty acid moieties of at least a portion of the fatty acid lower alkyl ester comprises fatty acids derived from butterfat.

12. The process of claim 1, wherein the fatty acid lower alkyl ester comprises homogeneous and heterogeneous fatty acids, and mixtures thereof.

13. The process of claim 1, wherein the reducing saccharide is selected from the group consisting of fructose, glucose, galactose, mannose, ribulose, rhamnose, xylulose, xylose, ribose, arabinose, sorbose, maltose, lactose, cellobiose, melibiose, and 4'-galactosyl lactose.

14. The process of claim 1, wherein the monohydric alcohol comprises an alkyl alcohol having from 1 to 24 carbons.

15. The process of claim 14, wherein the monohydric alcohol is selected from the group consisting of: methanol, ethanol, n-propanol, n-butanol, n-pentanol, n-octanol, n-decanol, n-dodecanol, n-tetradecanol, n-hexadecanol, and n-octadecanol.

16. The process of claim 1, wherein the alkyl moiety of the alkyl glycoside has from 1 to 24 carbons.

17. The process of claim 1, wherein the dihydric or trihydric alcohol is selected from the group consisting of: glycerol, 1,2-dihydroxy-($C_3$–$C_{24}$)-alkanes and hydroxyl group protected derivatives thereof having one free hydroxyl group.

18. The process of claim 1, wherein the tetrahydric alcohol is a tetrahydroxy-neopentane or a protected derivative thereof having one free hydroxyl group.

19. The process of claim 1, wherein the hydroxyl protecting groups are selected from the group consisting of isopropylidene groups, benzylidene groups and trityl groups.

20. A process for producing an alkyl glycoside fatty acid polyester comprising the steps of:

reacting a reducing saccharide with a monohydric alcohol, thereby forming an alkyl glycoside;

esterifying hydroxyl groups of the alkyl glycoside to form a lower acyl ester alkyl glycoside;

admixing the lower acyl ester alkyl glycoside, a fatty acid lower alkyl ester, and an interesterification catalyst to form a reaction mixture;

heating said reaction mixture to an elevated reaction temperature of at least 100° C. and maintaining the reaction temperature for a period of from one to three hours;

while maintaining the reaction temperature, drawing a vacuum of from about 0 to 10 torr over the reaction mixture to obtain a yield of at least 95% of an alkyl glycoside fatty acid polyester in the reaction mixture; and recovering an alkyl glycoside fatty acid polyester from the reaction mixture.

21. The process of claim 20, wherein the monohydric alcohol is selected from the group consisting of: methanol, ethanol, n-propanol, n-butanol, n-pentanol, n-octanol, n-decanol, n-dodecanol, n-tetradecanol, n-hexadecanol, and n-octadecanol.

22. A process for producing an alkyl glycoside fatty acid polyester comprising the steps of:

adding an alkyl glycoside to acetyl chloride, wherein the alkyl moiety of the alkyl glycoside is unsubstituted or is substituted by 1–3 protected hydroxyl groups, and allowing the alkyl glycoside and acetyl chloride to react at a temperature between about 30° C. and about 40° C., wherein at least about two equivalents of acetyl chloride is added per free hydroxyl group on said alkyl glycoside;

allowing an acetylation reaction to proceed for about 1–5 hours in a reaction mixture;

adding a lower alcohol to the reaction mixture;

neutralizing the reaction mixture with an aqueous solution of a base selected from the group consisting of sodium carbonate, sodium bicarbonate, ammonium bicarbonate, or potassium bicarbonate;

draining off the aqueous phase of the reaction mixture and washing with an aqueous solution;

azeotropically removing any remaining water;

removing remaining solvent under a vacuum of from about 0 to 10 torr leaving an acetyl alkyl glycoside product;

deprotecting any protected hydroxyl groups on the alkyl moiety;

contacting the acetyl alkyl glycoside product with a fatty acid lower alkyl ester in a ratio appropriate for interesterification with the acetyl alkyl glycoside;

adding an alkali metal catalyst to a mixture of the acetyl alkyl glycoside and the fatty acid methyl ester, and heating the mixture at a temperature above 95° C. for a period of from one to three hours to cause an interesterification reaction to occur;

applying a vacuum of from about 0 to 10 torr to obtain a yield of at least 95% of an alkyl glycoside fatty acid polyester in the reaction mixture; and isolating an alkyl glycoside fatty acid polyester product.

23. The process of claim 22, wherein said catalyst is potassium metal or sodium metal.

24. The process of claim 22, wherein said catalyst is a combination of an alkali metal carbonate and an alkali metal salt of a $C_4$–$C_{24}$ fatty acid.

25. The process of claim 22, wherein the lower alcohol is 1-butanol.

26. The process of claim 22, wherein the base is sodium bicarbonate.

27. The process of claim 22, wherein sodium metal is used as the catalyst in an amount of about 5% or less by weight.

28. The process of claim 22, wherein said temperature above 95° C. is from about 100° to about 125° C.

29. A process for producing an alkyl glycoside fatty acid polyester comprising the steps of:

reacting a lower acylated reducing saccharide halogenated at the anomeric carbon with a monohydric, dihydric, trihydric or tetrahydric alcohol having at least one free hydroxyl group, the remaining hydroxyl groups being protected with hydroxyl protecting groups, thereby forming a lower acyl ester alkyl glycoside;

removing any protecting groups on the alkyl moiety of the lower acyl ester alkyl glycoside;

admixing the lower acyl ester alkyl glycoside, a fatty acid lower alkyl ester, and an alkali metal catalyst to form a reaction mixture;

heating said reaction mixture to a reaction temperature in the range of from 100° to 125° C. and maintaining the reaction temperature for a period of from two to three hours;

while maintaining the reaction temperature, drawing a vacuum of from about 0 to 10 torr over the reaction mixture to obtain a yield of at least 95% of an alkyl glycoside fatty acid polyester in the reaction mixture; and recovering an alkyl glycoside fatty acid polyester from the reaction mixture.

* * * * *

UNITED STATES PATENT AND TRADEMARK OFFICE
CERTIFICATE OF CORRECTION

PATENT NO. : 5,550,220
DATED : August 27, 1996
INVENTOR(S) : R.S. Meyer et al.

Page 1 of 2

It is certified that error appears in the above-indentified patent and that said Letters Patent is hereby corrected as shown below:

On the title page, items:

[63]  Related U.S. Application Data Lines 8 & 9

", said Ser. No. 869,288, is a continuation of Ser. No. 347,264." should read --; and is also a continuation-in-part of (b) prior pending application Serial No. 532,926 filed June 4, 1990, which is a continuation of prior application Serial No. 347,264, filed May 3, 1989, now U.S. Patent No. 4,942,054, which was a continuation-in-part of prior application Serial No. 122,188, filed November 18, 1987, now U.S. Patent No. 4,840,815, which was a continuation-in-part of prior application Serial No. 049,625, filed May 13, 1987, now abandoned, the benefit of each filing date which is hereby claimed under 35 U.S.C. § 120.--

[56]  Refs. Cited (U.S. Pat. Docs.)

Insert the following reference:
--2,893,990  7/1959  Hass et al. . . . . . . . 536/119--

UNITED STATES PATENT AND TRADEMARK OFFICE
CERTIFICATE OF CORRECTION

PATENT NO. : 5,550,220
DATED : August 27, 1996
INVENTOR(S) : R.S. Meyer et al.

It is certified that error appears in the above-indentified patent and that said Letters Patent is hereby corrected as shown below:

[56]  Refs. Cited  "Manfield" should read --Mansfield--

Col.  Line
21    30    "wkh hydroxyl" should read --with hydroxyl--

Signed and Sealed this

Thirty-first Day of December, 1996

Attest:

BRUCE LEHMAN

Attesting Officer    Commissioner of Patents and Trademarks